US00PP09318P

United States Patent [19]

Hanes

[11] Patent Number: Plant 9,318

[45] Date of Patent: Oct. 3, 1995

[54] IVY GERANIUM NAMED 'FREESTYLE PINK'

[75] Inventor: Mitchell E. Hanes, Morgan Hill, Calif.

[73] Assignee: Goldsmith Seeds, Inc., Gilroy, Calif.

[21] Appl. No.: 368,527

[22] Filed: Jan. 4, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Henderson & Sturm

[57] ABSTRACT

A new ivy geranium cultivar particularly distinguished by green foliage without zonation, pink color, and semi-double flowers on large umbels, a vigorous plant that is fast rooting with a semi-compact habit.

1 Drawing Sheet

BACKGROUND OF THE NEW PLANT

The present invention comprises a new and distinct cultivar of geranium, botanically known as *Pelargonium peltatum,* and hereinafter referred to by the cultivar name Freestyle Pink. The new cultivar is propagated from a seedling resulting from the cross of a seed parent 1577-4 and the pollen parent, an ivy geranium known as Salmon Queen, a non-patented variety.

Freestyle Pink is a product of a planned breeding program intended to create new ivy geranium cultivars with pink colored flowers, semi-double flower from, mid-green foliage, vigorous growth and superior cutting productivity.

The new cultivar was created in 1990 in Gilroy, Calif. and has been repeatedly asexually reproduced by cuttings in Gilroy, Calif. and Guatemala over a 4 year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
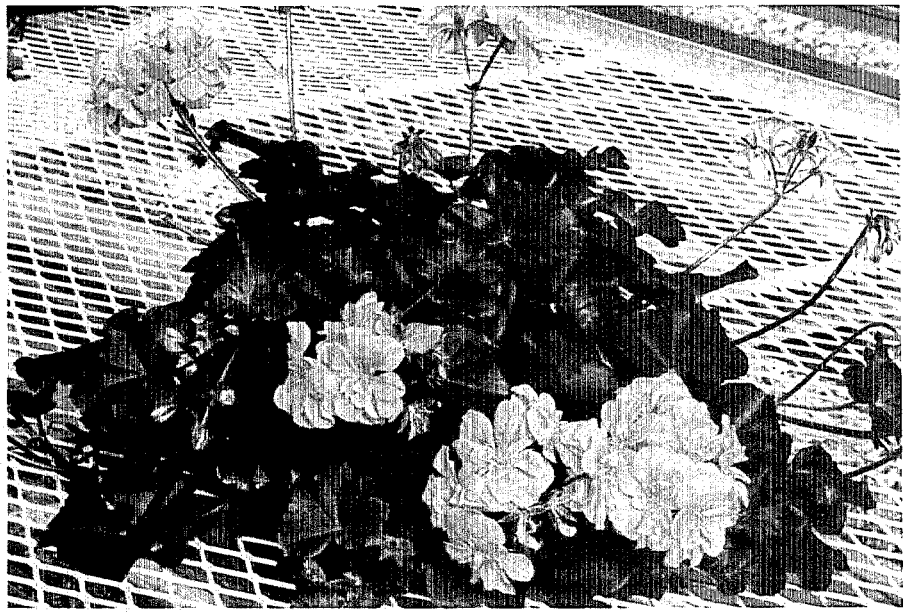
FIG. 1 shows overall plant habit.
Figure 2:
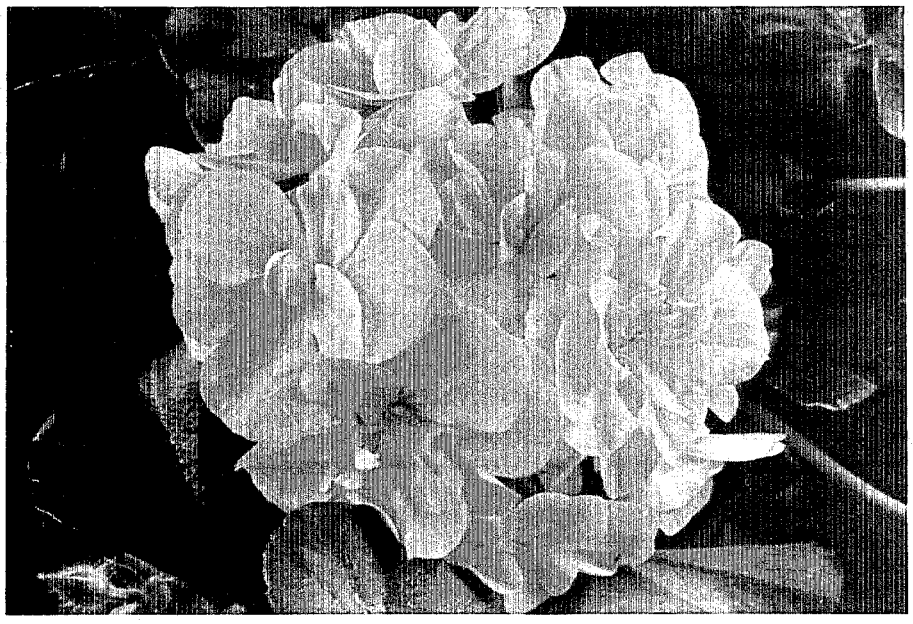
FIG. 2 illustrates the mature flower.

The following detailed descriptions set forth the distinctive characteristics of Freestyle Pink. The data which defines these characteristics were collected from asexual reproductions carried out by Goldsmith Seeds, Inc. in Gilroy, Calif. The plant history was taken on 16 week old plants, blossomed under natural light in a greenhouse and color readings were taken in the greenhouse (in Gilroy, Calif.) on Nov. 2, 1994 at 4:00 p.m. under ambient light. Color references are primarily to the R.H.S. Colour Chart of The Royal Horticultural Society of London (R.H.S.).

The Plant

Classification:

Botantical: *Pelargonium peltatum.*

Commercial: Ivy gernaium.

Form: Compact free branching.

Height: 8 cm, as a 6 inch pot plant, excluding blooms.

Growth: Rounded growth habit with short internodes.

Strength: Mid-green shiny foliage on a plant that has some resistance to edema. Good shipping ability as rooted or unrooted cuttings.

Foliage: Abundant quantity.

*Leaves.*—Size: Diameter about 7.5 cm. Shape: Ivy-shaped leaf with edges raised above the plant of the center of the leaf. Margin: Smooth. Texture: Waxy on both surfaces. Ribs: Radiate from the point of attachment of the petiole. Veins: Present but very inconspicuous. Color: Upper side: Darker green generally without a ring shaped zone circling the center of the leaf. However, on the young leaves such a zone is sometimes present. Under side: Lighter green color without zonation. Veins a little more distinct than on the upper leaf surface. Petioles: About 4–4.5 cm in length on a mature leaf.

The Bud

Size:

*Diameter.*—About 7 mm.

*Length.*—About 1.2–2.0 cm at time of bud opening.

Shape: Pointed ovoid.

Color: Petals when sepals first divide, 55A R.H.S.

Sepals: 5 in number, flat behind petals. Pointed linear lanceolate, 137C R.H.S. in an open flower.

The Flower

Blooming habit: Continuous throughout the year.

Size: Approximately 4.8 cm diameter, 1.3 cm deep.

Form: Semi-double.

Petals: Color 55A-B R.H.S. Approximately 12 imbricate outer petals, 1.8–2.0 cm wide and approximately 2.9 cm long. Six to eight inner smaller petaloids of varying shape. Both the outer petals and inner petaloids are pink from the base of the petal to the outer margin. The two top petals have a feather vein pattern that is (a darker red-pink color) 57B R.H.S. Veins slightly darker than interveinal regions. Color changing little with age. Underside of petals lighter. Petals and petaloids soft and satiny.

Pedicel: Approximately 2.6 cm in length.

Persistence: Non-shattering flower.

Inflorescence

Type: An umbel composed of approximately 7–11 flowers, erect or laterally ascending.

Peduncle: Approximately 12 cm in length, green without pigmentation.

Reproductive Organs

Stamens:

*Anthers.*—7–8 positioned at or below the mature stigma, dull red prior to anthesis.

*Filaments.*—White near base and mid length, graduating to dull red near anther.

*Pollen.*—Orange in color.

Pistil:

*Number.*—1.

*Length.*—Approximately 10 mm.

*Stigma.*—5 linear lobes of near equal length, curling back toward ovary, purplish-red.

*Style.*—Length: About 4 mm. Color: White.

*Ovaries.*—At anthesis, densely pubescent with white hairs, oblong. Green drying to a light brown at maturity.

*Fruit.*—Partially fertile.

I claim:

1. A new and distinct cultivar of ivy geranium substantially as herein shown and described, named Freestyle Pink, that is characterized by: green foliage without zonation, pink color, and semi-double flowers on large umbels, a vigorous plant that is fast rooting with a semi-compact habit.

* * * * *